United States Patent [19]
Brewer et al.

[11] Patent Number: 5,902,323
[45] Date of Patent: May 11, 1999

[54] METHOD AND APPARATUS FOR EXTERNAL DEFIBRILLATION USING A DEVICE HAVING A LOW CAPACITANCE AND SMALL TIME CONSTANT

[75] Inventors: James E. Brewer, Cottage Grove, Minn.; Charles D. Swerdlow, Los Angeles, Calif.

[73] Assignee: SurVivaLink Corporation, Minneapolis, Minn.

[21] Appl. No.: 08/832,710

[22] Filed: Apr. 11, 1997

Related U.S. Application Data

[XX .
[60] Provisional application No. 60/015,361, Apr. 12, 1996, abandoned.

[51] Int. Cl.⁶ .................................................... A61N 1/39
[52] U.S. Cl. ........................................................... 607/5
[58] Field of Search ............................................ 607/5–8

[56] References Cited

U.S. PATENT DOCUMENTS

| | | |
|---|---|---|
| 4,768,512 | 9/1988 | Imran . |
| 5,385,575 | 1/1995 | Adams . |
| 5,391,186 | 2/1995 | Kroll et al. . |
| 5,431,686 | 7/1995 | Kroll et al. . |
| 5,468,254 | 11/1995 | Hahn et al. . |
| 5,593,427 | 1/1997 | Gilner et al. . |
| 5,601,612 | 2/1997 | Gilner et al. . |
| 5,607,454 | 3/1997 | Cameron et al. . |

FOREIGN PATENT DOCUMENTS

| | | |
|---|---|---|
| WO 95/09673 | 4/1995 | European Pat. Off. . |
| WO 95/32020 | 11/1995 | European Pat. Off. . |

OTHER PUBLICATIONS

The Journal of General Physiology, Rockefeller Institute for Medical Research, vol. 15, pp. 731–755, 1932.
Pacing and Clinical Electrophysiology, Futura Publishing Co., vol. 18, No. 4, pp. 633–758, Apr. 1995.
Journal of Cardiovascular Electrophysiology, Futura Publishing Co., vol. 6, No. 9, Sep. 1995.
Pacing and Clinical Electrophysiology, Futura Publishing Co., vol. 18, No. 3, Part II, pp. 505–631, Mar. 1995.
Pacing and Clinical Electrophysiology, Futura Publishing Co., vol. 19, No. 8, pp. 1141–1272, Aug. 1996.
Pacing and Clinical Electrophysiology, Futura Publishing Co., vol. 17, No. 11, Part I, pp. 1707–1836, Nov. 1994.
The Journal of General Physiology, Rockefeller Institute for Medical Research, vol. 15, pp. 708–729, 1932.
Journal of the American College of Cardiology, American College of Cardiology, vol. 13, No. 1, Jan. 1989.
Pacing and Clinical Electrophysiology, Futura Publishing Co., vol. 16, No. 4, Part I, pp. 693–827, Apr. 1993
Circulation, American Heart Association, vol. 82, No. 6, pp. 2128–2141, Dec. 1990.
Circulation, American Heart Association, vol. 76, No. 5, pp. 1176–1184, Nov. 1987.
Circulation, American Heart Associate, vol. 91, No. 6, pp. 1768–1774, Mar. 1995.
Circulation, American Heart Association, vol. 92, No. 6, pp. 1634–1643, Sep. 1995.
Circulation, American Heart Associate, vol. 94, No. 10, pp. 2507–2514, Nov. 1996.

*Primary Examiner*—William E. Kamm
*Attorney, Agent, or Firm*—Patterson & Keough, P.A.

[57] ABSTRACT

A method and apparatus for delivering a truncated damped sinusoidal external defibrillation waveform which, when applied through a plurality of electrodes positioned on a patient's torso will produce a desired response in the patient's cardiac cell membranes is provided. The external defibrillator is utilized for applying a damped sinusoidal waveform having a first waveform phase and a second waveform phase to a pair of electrodes. The external defibrillator has a first capacitive component, a first inductive component, a first truncating switch, and waveform control circuitry. The waveform control circuitry of the defibrillator controls the first and second truncating switches such that the duration of the second phase waveform delivered by the second charge storage component is greater than the duration of the first phase waveform delivered by the first charge storage component.

27 Claims, 6 Drawing Sheets

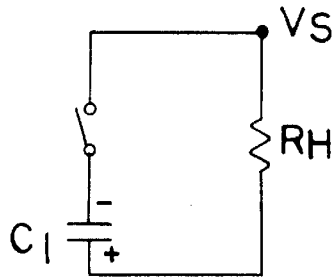
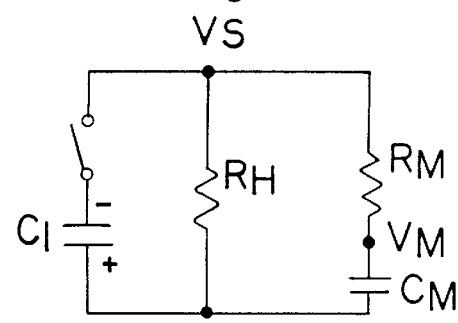
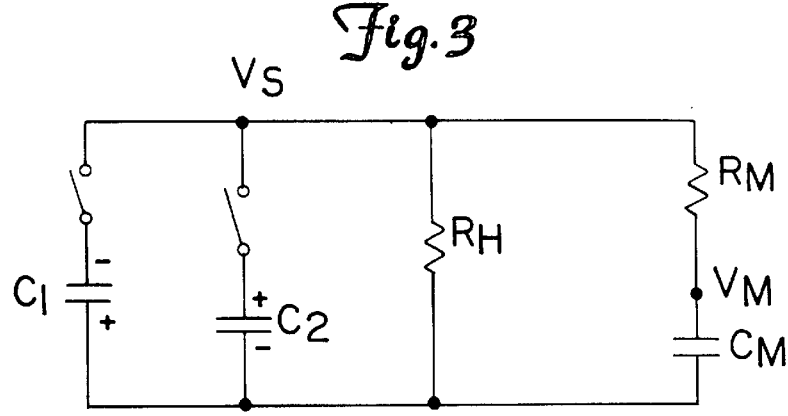
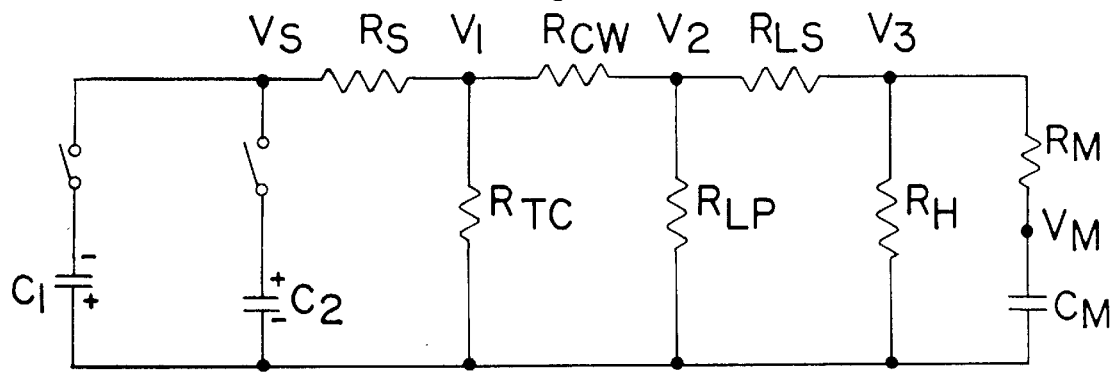

METHOD AND APPARATUS FOR EXTERNAL DEFIBRILLATION USING A DEVICE HAVING A LOW CAPACITANCE AND SMALL TIME CONSTANT

RELATED APPLICATIONS

This application is based on provisional patent application Ser. No. 60/015,361, filed Apr. 12, 1996 entitled METHOD OF DESIGNING EXTERNAL DEFIBRILLATOR WAVEFORMS, now abandoned the contents of which are herein incorporated by reference and priority back to the Apr. 12, 1996 filing date is hereby claimed.

FIELD OF THE INVENTION

This invention relates generally to an electrotherapy method and apparatus for delivering an electrical pulse to a patient's heart. In particular, this invention relates to a method and apparatus for creating an electrical waveform delivered by an external defibrillator based on theory and practice as described herein.

BACKGROUND OF THE INVENTION

Devices for defibrillating a heart have been known for sometime now. Implantable defibrillators are well accepted by the medical community as effective tools to combat fibrillation for an identified segment of the population. A substantial amount of research in fibrillation and the therapy of defibrillation has been done. Much of the most recent research has concentrated on understanding the effects that a defibrillation shock pulse has on fibrillation to terminate such a condition.

A monophasic waveform is defined to be a single phase, capacitive-discharge, time-truncated, waveform with exponential decay. A biphasic waveform is defined to comprise two monophasic waveforms, separated by time and of opposite polarity. The first phase is designated $\phi_1$ and the second phase is designated $\phi_2$. The delivery of $\phi_1$ is completed before the delivery of $\phi_2$ is begun.

After extensive testing, it has been determined that biphasic waveforms are more efficacious than monophasic waveforms. There is a wide debate regarding the reasons for the increased efficacy of biphasic waveforms over that of a monophasic waveforms. One hypothesis holds that $\phi_1$ defibrillates the heart and $\phi_2$ performs a stabilizing action that keeps the heart from refibrillating.

Biphasic defibrillation waveforms are now the standard of care in clinical use for defibrillation with implantable cardioverter-defibrillators (ICDs), due to the superior performance demonstrated over that of comparable monophasic waveforms. To better understand these significantly different outcomes, ICD research has developed cardiac cell response models to defibrillation. Waveform design criteria have been derived from these first principles and have been applied to monophasic and biphasic waveforms to optimize their parameters. These principles-based design criteria have produced significant improvements over the current art of waveforms.

In a two paper set, Blair developed a model for the optimal design of a monophasic waveform when used for electrical stimulation. (1) Blair, H. A., "On the Intensity-time relations for stimulation by electric currents." I. J. Gen. Physiol. 1932; 15: 709–729. (2) Blair, H. A., "On the Intensity-time Relations for stimulation by electric currents. II. J. Gen. Physiol. 1932; 15: 731–755. Blair proposed and demonstrated that the optimal duration of a monophasic waveform is equal to the point in time at which the cell response to the stimulus is maximal. Duplicating Blair's model, Walcott extended Blair's analysis to defibrillation, where they obtained supporting experimental results. Walcott, et al., "Choosing the optimal monophasic and biphasic waveforms for ventricular defibrillation." J. Cardiovasc Electrophysiol. 1995; 6: 737–750.

Independently, Kroll developed a biphasic model for the optimal design of $\phi_2$ for a biphasic defibrillation waveform. Kroll, M. W., "A minimal model of the single capacitor biphasic defibrillation waveform." PACE 1994; 17:1782–1792. Kroll proposed that the $\phi_2$ stabilizing action removed the charge deposited by $\phi_1$ from those cells not stimulated by $\phi_1$. This has come to be known as "charge burping". Kroll supported his hypothesis with retrospective analysis of studies by Dixon, et al., Tang, et al., and Freese, et al. regarding single capacitor, biphasic waveform studies. Dixon, et al., "Improved defibrillation thresholds with large contoured epicardial electrodes and biphasic waveforms." Circulation 1987; 76:1176–1184; Tang, et al. "Ventricular defibrillation using biphasic waveforms: The Importance of Phasic duration." J. Am. Coll. Cardiol. 1989; 13:207–214; and Feeser, S. A., et al. "Strength-duration and probability of success curves for defibrillation with biphasic waveforms." Circulation 1990; 82:2128–2141. Again, the Walcott group retrospectively evaluated their extension of Blair's model to $\phi_2$ using the Tang and Feeser data sets. Their finding further supported Kroll's hypothesis regarding biphasic defibrillation waveforms. For further discussions on the development of these models, reference may be made to PCT publications WO 95/32020 and WO 95/09673 and to U.S. Pat. No. 5,431,686.

The charge burping hypothesis can be used to develop equations that describe the time course of a cell's membrane potential during a biphasic shock pulse. At the end of $\phi_1$, those cells that were not stimulated by $\phi_1$ have a residual charge due to the action of $\phi_1$ on the cell. The charge burping model hypothesizes that an optimal pulse duration for $\phi_2$ is that duration that removes as much of the $\phi_1$ residual charge from the cell as possible. Ideally, these unstimulated cells are set back to "relative ground." The charge burping model proposed by Kroll is based on the circuit model shown in FIG. 2b which is adapted from the general model of a defibrillator illustrated in FIG. 2a.

The charge burping model also accounts for removing the residual cell membrane potential at the end of a $\phi_1$ pulse that is independent of a $\phi_2$. That is, $\phi_2$ is delivered by a set of capacitors separate from the set of capacitors used to deliver $\phi_1$. This charge burping model is constructed by adding a second set of capacitors, as illustrated in FIG. 3. In this figure, $C_1$ represents the $\phi_1$ capacitor set, $C_2$ represents the $\phi_2$ capacitor set $R_H$ represents the resistance of the heart, and the pair $C_M$ and $R_M$ represent membrane series capacitance and resistance of a single cell. The node $V_S$ represents the voltage between the electrodes, while $V_M$ denotes the voltage across the cell membrane.

External defibrillators send electrical pulses to the patient's heart through electrodes applied to the patient's torso. External defibrillators are useful in any situation where there may be an unanticipated need to provide electrotherapy to a patient on short notice. The advantage of external defibrillators is that they may be used on a patient as needed, then subsequently moved to be used with another patient.

However, this important advantage has two fundamental limitations. First, external defibrillators do not have direct contact with the patient's heart. External defibrillators have traditionally delivered their electrotherapeutic pulses to the patient's heart from the surface of the patient's chest. This is known as the transthoracic defibrillation problem. Second, external defibrillators must be able to be used on patients having a variety of physiological differences. External defibrillators have traditionally operated according to pulse amplitude and duration parameters that can be effective in all patients. This is known as the patient variability problem.

The prior art described above effectively models implantable defibrillators, however it does not fully addressed the transthoracic defibrillation problem nor the patient variability problem. In fact, these two limitations to external defibrillators are not fully appreciated by those in the art. For example, prior art disclosures of the use of truncated exponential monophasic or biphasic shock pulses in implantable or external defibrillators have provided little guidance for the design of an external defibrillator that will successfully defibrillate across a large, heterogeneous population of patients. In particular, an implantable defibrillator and an external defibrillator can deliver a shock pulse of similar form, and yet the actual implementation of the waveform delivery system is radically different.

In the past five years, new research in ICD therapy has developed and demonstrated defibrillation models that provide waveform design rules from first principles. These defibrillation models and their associated design rules for the development of defibrillation waveforms and their characteristics were first developed by Kroll and Irnich for monophasic waveforms using effective and rheobase current concepts. (1) Kroll, M. W., "A minimal model of the monophasic defibrillation pulse." PACE 1993; 15: 769. (2) Irnich, W., "Optimal truncation of defibrillation pulses." PACE 1995; 18: 673. Subsequently, Kroll, Walcott, Cleland and others developed the passive cardiac cell membrane response model for monophasic and biphasic waveforms, herein called the cell response model. (1) Kroll, M. W., "A minimal model of the single capacitor biphasic defibrillation waveform." PACE 1994; 17: 1782. (2) Walcott, G. P., Walker, R. G., Cates. A. W., Krassowska, W., Smith, W. M, Ideker RE. "Choosing the optimal monophasic and biphasic waveforms for ventricular defibrillation." J Cardiovasc Electrophysiol 1995; 6:737; and Cleland B G. "A conceptual basis for defibrillation waveforms." PACE 1996; 19:1186).

A significant increase in the understanding of waveform design has occurred and substantial improvements have been made by using these newly developed design principles. Block et al. has recently written a comprehensive survey of the new principles-based theories and their impact on optimizing internal defibrillation through improved waveforms. Block M, Breithardt G., "Optimizing defibrillation through improved waveforms." PACE 1995; 18:526.

There have not been significant developments in external defibrillation waveforms beyond the two basic monophasic waveforms: the damped sine or the truncated exponential. To date, their design for transthoracic defibrillation has been based almost entirely on empirically derived data. It seems that the design of monophasic and biphasic waveforms for external defibrillation has not yet been generally influenced by the important developments in ICD research.

Recently there has been reported research on the development and validation of a biphasic truncated exponential waveform in which it was compared clinically to a damped sine waveform. For additional background, reference may be made to U.S. Pat. Nos. 5,593,427, 5,601,612 and 5,607,454. See also: Gliner B E, Lyster T E, Dillon S M, Bardy G H, "Transthoracic defibrillation of swine with monophasic and biphasic waveforms." Circulation 1995; 92:1634–1643; Bardy G H, Gliner B E, Kudenchuk P J, Poole J E, Dolack G L, Jones G K, Anderson J, Troutman C, Johnson G.; "Truncated biphasic pulses for transthoracic defibrillation." Circulation 1995; 91:1768–1774; and Bardy G H et al, "For the Transthoracic Investigators. Multicenter comparison of truncated biphasic shocks and standard damped sine wave monophasic shocks for transthoracic ventricular defibrillation." Circulation 1996; 94:2507–2514. Although the research determined a usable biphasic waveform, there was no new theoretical understanding determined for external waveform design. It appears that external waveform research may develop a "rules-of-thumb by trial and error" design approach much like that established in the early stages of theoretical ICD research. The noted limitations of the transthoracic biphasic waveform may be due in part to a lack of principles-based design rules to determine its waveform characteristics.

Monophasic defibrillation waveforms remain the standard of care in clinical use for transthoracic defibrillation. Waveform design has not yet been influenced by the important gains made in ICD research. The limitations of present transthoracic waveforms may be due in part to a lack of application of these design principles to determine optimal waveform characteristics. To overcome these limitations, design principles and design rules based on cell response have recently been developed for external defibrillation waveforms. The transthoracic model incorporates elements into a cell response model that extends it to external defibrillation.

There is a continued need for an apparatus and methodology for accurately designing an external defibrillator waveform to optimally determine waveform characteristics for any type of external defibrillator waveform.

High resistance patients, such as those patients receiving transchest external defibrillation, are not well served by low capacitor, biphasic defibrillation waveforms wherein the duration of phase one of the waveform is greater than or equal to the duration of phase two. There is a need in the industry to better serve such patients.

SUMMARY OF THE INVENTION

The present invention relates to an external defibrillation method and apparatus that addresses the limitations in the prior art. The present invention incorporates three singular practices that distinguish the practice of designing external defibrillators from the practice of designing implantable defibrillators. These practices are 1) designing multiphasic transthoracic shock pulse waveforms from principles based on cardiac electrophysiology, 2) designing multiphasic transthoracic shock pulse waveforms in which each phase of the waveform can be designed without implementation limitations placed on its charging and delivery means by such means for prior waveform phases, and 3) designing multiphasic transthoracic shock pulse waveforms to operate across a wide range of parameters determined by a large, heterogeneous population of patients.

In particular, the present invention provides for a method and apparatus for determining an optimal transchest external defibrillation waveform which, when applied through a plurality of electrodes positioned on a patient's torso will produce a desired response in the patient's cardiac cell membranes. The method includes the steps of determining and providing a quantitative description of the desired cardiac membrane response function. A quantitative model of a defibrillator circuit for producing external defibrillation waveforms is then provided. Also provided is a quantitative model of a patient which includes a chest component, a heart component and a cell membrane component. Finally, a quantitative description of a transchest external defibrillation waveform that will produce the desired cardiac membrane response function is computed. The computation is made as a function of the desired cardiac membrane response function, the patient model and the defibrillator circuit model.

BRIEF DESCRIPTION OF THE DRAWINGS

FIG. 2a is a very simplified defibrillator model.

FIG. 2b is a known monophasic defibrillation model.

FIG. 3 is a known biphasic defibrillation model.

FIG. 4 represents a monophasic or biphasic capacitive-discharge external defibrillation model according to the present invention.

DESCRIPTION OF THE PREFERRED EMBODIMENT

The present invention provides a method and apparatus for determining an optimal transchest external defibrillation waveform which, when applied through a plurality of electrodes positioned on a patient's torso will provide a desired response in the patient's cardiac cell membrane.

Figure 1A:
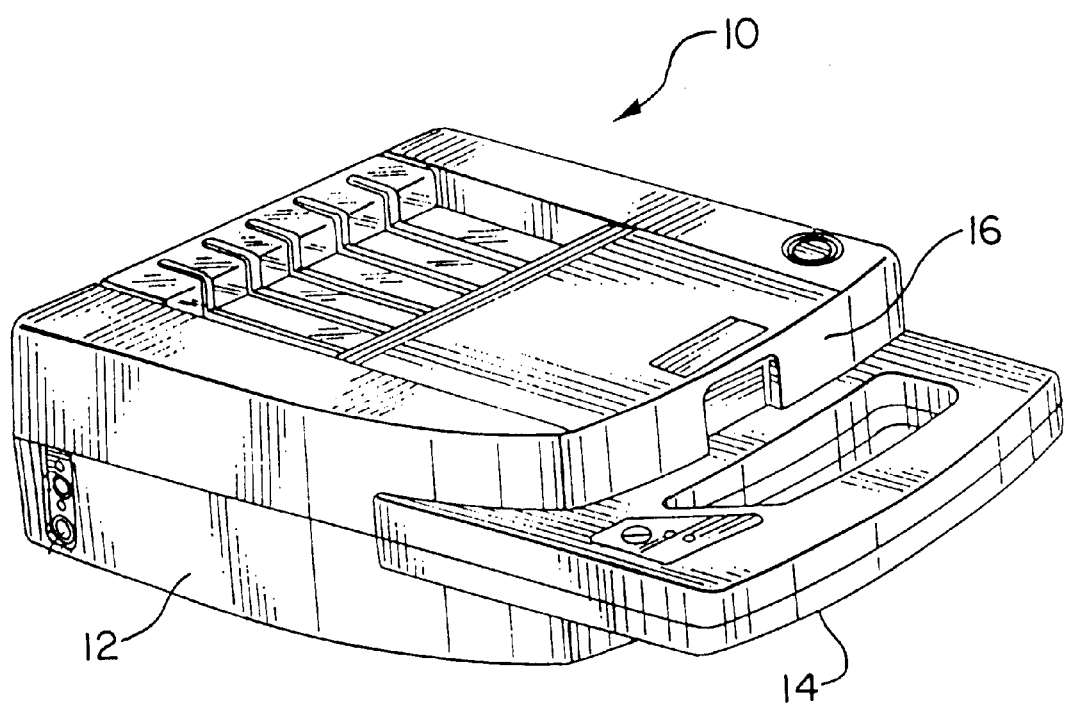
FIGS. 1a and 1b are perspective views of an AED according to the present invention.
Figure 1B:
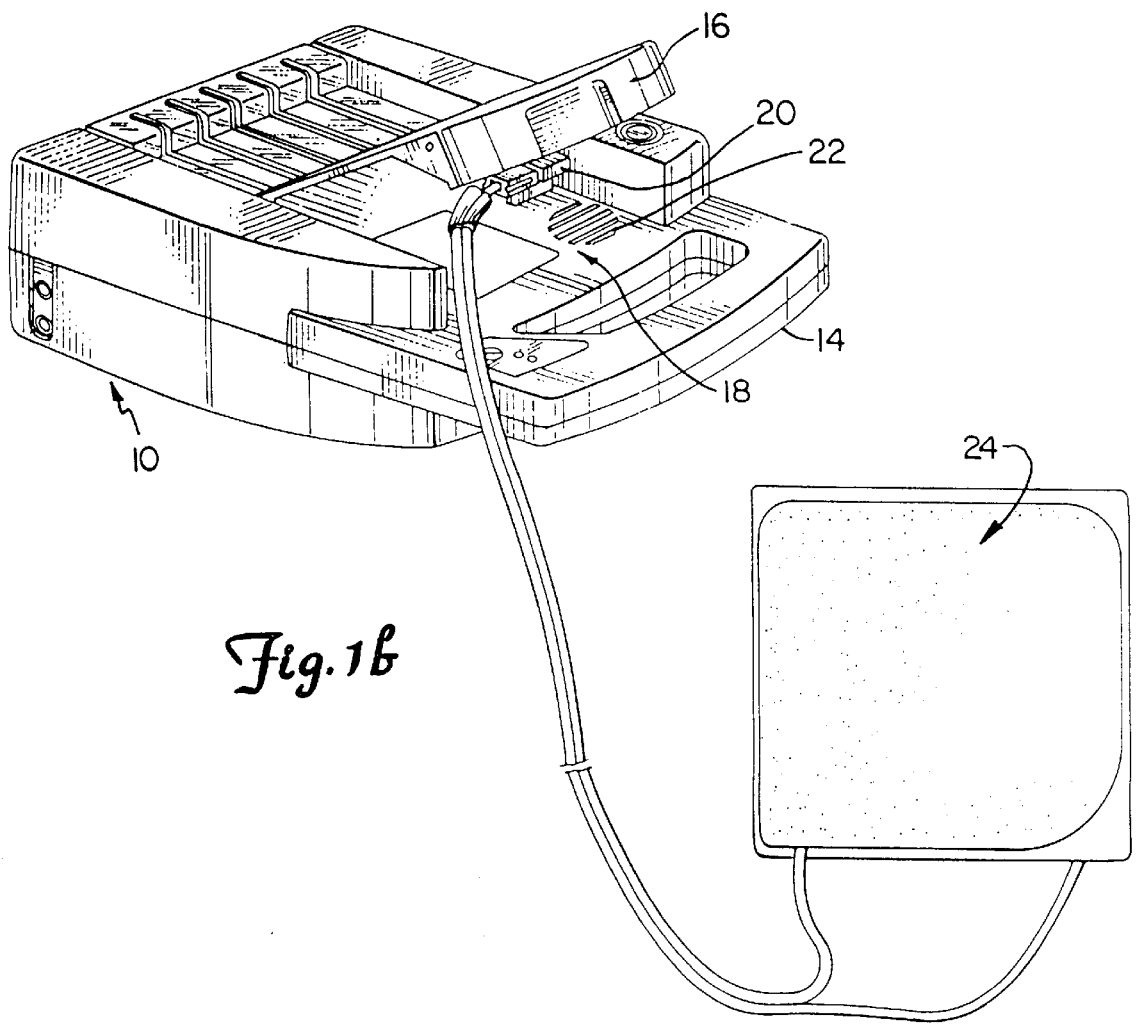

The apparatus of the present invention is an automated external defibrillator (AED) illustrated in FIGS. 1a and 1b. FIG. 1a illustrates an AED 10, including a plastic case 12 with a carrying handle 14. A lid 16 is provided which covers an electrode compartment 18. An electrode connector 20, a speaker 22 and a diagnostic panel (not shown) are located on case 12 within electrode compartment 18. FIG. 1b illustrates AED 10 having a pair of electrodes 24 connected thereto. Electrodes 24 can be pre-connected to connector 20 and stored in compartment 18.

The operation of AED 10 is described briefly below. A rescue mode of AED 10 is initiated when lid 16 is opened to access electrodes 24. The opening of lid 16 is detected by AED 10 to effectively turn on the device. AED 10 then quickly runs a short test routine. After electrodes 24 have been placed on the patient, AED 10 senses patient specific parameters, such as the impedance of the patient. The patient specific parameters are then utilized in the design of optimal waveforms as will be described below.

If a shockable condition is detected through electrodes 24, a plurality of capacitors inside of AED 10 are charged from an energy source, typically a detachable battery pack. Based upon the patient specific parameters sensed, the duration and other characteristics of a discharge waveform are then calculated. The energy stored in AED 10 is then discharged to the patient through electrodes 24.

For a more detailed description of the physical structure of AED 10 or the process involved in sensing, charging, shocking and testing, reference should be made to applicants co-pending application Ser. No. 08/512,441, filed Aug. 8, 1995 entitled AUTOMATED EXTERNAL DEFIBRILLATOR WITH SELF-TEST SYSTEM which is assigned to the assignee of the present invention, the disclosure of which is herein incorporated by reference.

In the present invention it is not assumed that both phases of a biphasic waveform are delivered using the same set of capacitors or that both phases of a biphasic waveform are delivered using the capacitor set in the same electrical configuration, although such an embodiment is considered within the spirit and scope of the present invention.

Transthoracic defibrillation is generally performed by placing electrodes on the apex and anterior positions of the chest wall. With this electrode arrangement, nearly all current passing through the heart is conducted by the lungs and the equipotential surfaces pass through the myocardium normal to the electrode axis. The present invention uses the transthoracic charge burping model to develop design equations that describe the time course of a cell's membrane potential during a transthoracic biphasic shock pulse. These equations are then used to create equations that describe the design of monophasic and biphasic shock pulses for transchest defibrillation to optimize the design of $\phi_1$ for defibrillating and the design of $\phi_2$ for stabilizing. These optimizing shock pulse design equations are called design rules.

According to the present invention, the main series pathway for current is to pass through the chest wall, the lungs, and the heart. Additionally, there are two important shunting pathways in parallel with the current pathway through the heart. These shunting pathways must be taken into consideration. The lungs shunt current around the heart through a parallel pathway. The second shunting pathway is provided by the thoracic cage. The resistivity of the thoracic cage and the skeletal muscle structure is low when compared to lungs. The high resistivity of the lungs and the shunting pathways are characterizing elements of external defibrillation that distinguish the art from intracardiac defibrillation and implantable defibrillation technologies.

Therefore, in the transthoracic defibrillation model of the present invention illustrated in FIG. 4, there are several resistances in addition to those discussed for the charge burping model above. $R_S$ represents the resistance of the defibrillation system, including the resistance of the defibrillation electrodes. $R_{CW}$ and $R_{LS}$ represent the resistances of the chest wall and the lungs, respectively, in series with resistance of the heart, $R_H$. $R_{TC}$ and $R_{LP}$ represent the resistances of the thoracic cage and the lungs, respectively, in parallel with the resistance of the heart.

The design rules for external defibrillation waveforms are determined in three steps. In the first step, the transchest forcing function is determined. The transchest forcing function is the name that is given to the voltage that is applied across each cardiac cell during an external defibrillation shock. In the second step, the design equations for $\phi_1$ of a shock pulse are determined. The design equations are the equations describing the cell's response to the $\phi_1$ transchest forcing function, the equation describing the optimal $\phi_1$ pulse duration, and the equation describing the optimal $\phi_1$ capacitor. Therefore, step two relates the cell response to the action of a monophasic shock pulse or the first phase of a biphasic shock pulse. This relation is used to determine the optimal design rules and thereby design parameters for the implementation of this phase in an external defibrillator. It will be clear to those in the art that step two is not restricted to capacitor discharge shock pulses and their associated transchest forcing function. Another common implementation of an external defibrillator incorporates a damped sine wave for a shock pulse and can be either a monophasic or biphasic waveform. This type of external defibrillator is modeled by the circuit shown in FIG. 5. In the third step, the design equations for $\phi_2$ of a shock pulse are determined. The design equations are the equations describing the cell's response to the $\phi_2$ transchest forcing function, the equation describing the optimal $\phi_2$ pulse duration and the equation describing the optimal $\phi_2$ capacitor. These design equations are employed to determine the optimal design rules and thereby design parameters of $\phi_2$ of a biphasic shock pulse with respect to how the cell responds to the shock pulse. An important element of this invention is to provide shock pulse waveforms that are designed from a cardiac cell response model developed from first principles and that correctly determines the effects of the chest and its components on the ability of a shock pulse to defibrillate.

The transchest forcing function is determined by solving for the voltage found at node $V_3$ in FIG. 4. The transchest forcing function is derived by solving for $V_3$ using the following three nodal equations:

$$\frac{V_1 - V_S}{R_S} + \frac{V_1}{R_{TC}} + \frac{V_1 - V_2}{R_{CW}} = 0, \tag{1}$$

$$\frac{V_2 - V_1}{R_{CW}} + \frac{V_2}{R_{LP}} + \frac{V_2 - V_3}{R_{LS}} = 0, \text{ and} \tag{2}$$

$$\frac{V_3 - V_2}{R_{LS}} + \frac{V_3}{R_H} + \frac{V_3 - V_M}{R_M} = 0. \tag{3}$$

Equation 1 can be rewritten as $$V_1\left(\frac{1}{R_S} + \frac{1}{R_{TC}} + \frac{1}{R_{CW}}\right) = \frac{V_S}{R_S} + \frac{V_2}{R_{CW}}. \tag{4A}$$

$$V_1 = \frac{V_S}{R_S \Omega_1} + \frac{V_2}{R_{CW} \Omega_1}, \text{ where} \tag{4B}$$

$$\Omega_1 = \frac{1}{R_S} + \frac{1}{R_{TC}} + \frac{1}{R_{CW}}.$$

Rewriting equation 2, we have $$V_2\left(\frac{1}{R_{CW}} + \frac{1}{R_{LP}} + \frac{1}{R_{LS}}\right) = \frac{V_1}{R_{CW}} + \frac{V_3}{R_{LS}}. \tag{4C}$$

By substituting equation 4B for $V_1$ into equation 4C, we can solve for $V_2$ as an expression of $V_S$ and $V_3$:

$$V_2 = \frac{V_S}{R_S R_{CW} \Omega_1 \Omega_2 \Omega_{22}} + \frac{V_3}{R_{LS} \Omega_2 \Omega_{22}}, \text{ where} \tag{5}$$

$$\Omega_2 = \frac{1}{R_{LS}} + \frac{1}{R_{LP}} + \frac{1}{R_{CW}}, \text{ and}$$

$$\Omega_{22} = 1 - \frac{1}{R_{CW}^2 \Omega_1 \Omega_2}.$$

Now solving for $V_3$ as an expression of $V_S$ and $V_M$, equation 3 may be rearranged as $$V_3\left(\frac{1}{R_{LS}} + \frac{1}{R_H} + \frac{1}{R_M}\right) = \frac{V_2}{R_{LS}} + \frac{V_M}{R_M} \tag{6}$$

so that $$V_3 = \frac{V_2}{R_{LS}\Omega_3} + \frac{V_M}{R_M\Omega_3} \tag{7}$$

where $$\Omega_3 = \frac{1}{R_{LS}} + \frac{1}{R_H} + \frac{1}{R_M}.$$

Substituting equation 5 for $V_2$ into equation 7, we can solve for $V_3$ as an expression of $V_S$ and $V_M$:

$$V_3 = \frac{V_S}{R_S R_{CW} R_{LS} \Omega_1 \Omega_2 \Omega_{22} \Omega_3 \Omega_{33}} + \frac{V_M}{R_M \Omega_3 \Omega_{33}} \tag{8}$$

where $$\Omega_{33} = 1 - \frac{1}{(R_{LS}^2 \Omega_2 \Omega_{22} \Omega_3)} \tag{9}$$

From equation 8 we define $\Omega_M$ to be:

$$\Omega_M = R_M \Omega_3 \Omega_{33} = R_M \Omega_3 \left(1 - \frac{1}{(R_{LS}^2 \Omega_2 \Omega_{22} \Omega_3)}\right) \tag{10}$$

$$\Omega_M = R_M\left(\Omega_3 - \frac{1}{R_{LS}^2\left(\Omega_2 - \frac{1}{R_{CW}^2 \Omega_1}\right)}\right).$$

Figure 5A:
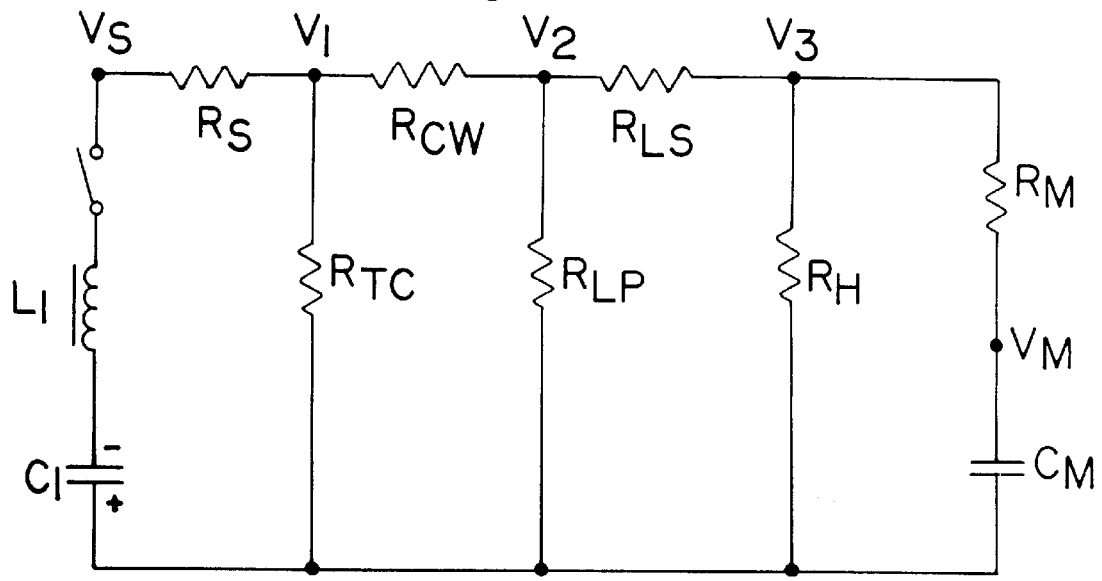
FIG. 5A represents a monophasic capacitor-inductor external defibrillator model according to the present invention.
Figure 5B:
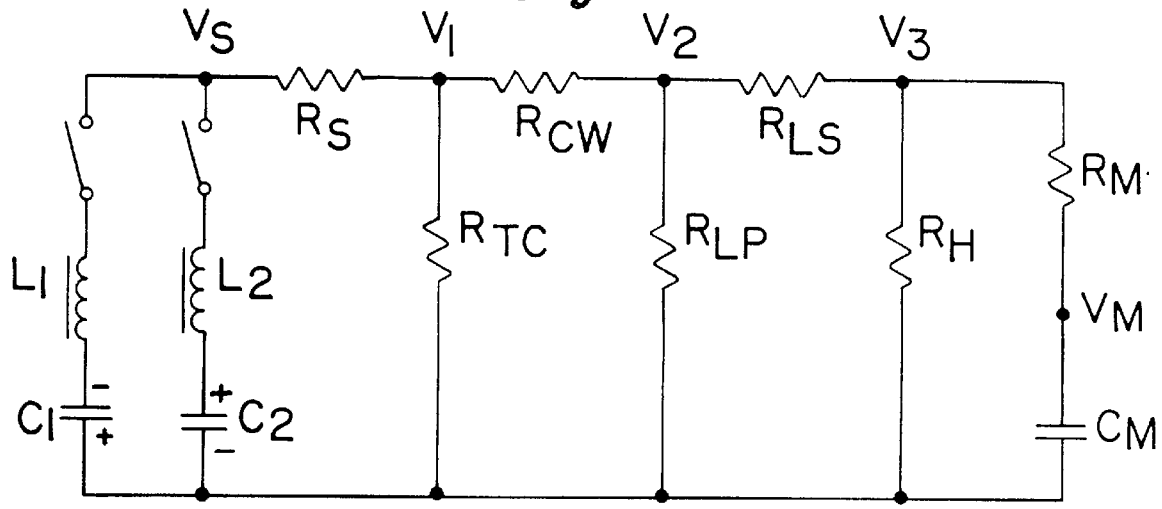
FIG. 5B represents an alternative embodiment of a biphasic capacitor-inductor external defibrillator model according to the present invention.

From equation 8 we also define $\Omega_S$ to be:

$$\Omega_S = R_S R_{CW} R_{LS} \Omega_1 \Omega_2 \Omega_3 \Omega_{22} \Omega_{33} \tag{11}$$

$$\Omega_S = R_S R_{CW} R_{LS} \Omega_1 \Omega_2\left(1 - \frac{1}{(R_{CW}^2 \Omega_1 \Omega_2)}\right)\Omega_3\left(1 - \frac{1}{(R_{LS}^2 \Omega_2 \Omega_{22} \Omega_3)}\right) \tag{12}$$

$$\Omega_S = R_S R_{CW} R_{LS}\left(\Omega_1 \Omega_2 - \frac{1}{R_{CW}^2}\right)\left(\Omega_3 - \frac{1}{R_{LS}^2\left(\Omega_2 - \frac{1}{R_{CW}^2 \Omega_1}\right)}\right) \tag{13}$$

so that $$V_3 = \frac{V_S}{\Omega_S} + \frac{V_M}{\Omega_M} \tag{14}$$

is the general transchest transfer function as shown in FIG. 4 or FIGS. 5A and 5B. Equation 14 incapsulates the transchest elements and their association between the forcing function $V_S$ (which models a defibrillation circuit and the shock pulse) and the cell membrane voltage $V_M$. Therefore, this completes the first step.

The variable $V_S$ may now be replaced with a more specific description of the defibrillation circuitry that implements a shock pulse. For a first example, a monophasic time-truncated, capacitive-discharge circuit may be represented by $V_S = V_1 e^{-t/\tau_1}$, where $V_1$ is the leading-edge voltage for the shock pulse and $\tau_1 = RC_1$, with R determined below.

As shown in FIGS. 5A and 5B, a second example would be a monophasic damped sine wave circuit, represented by $$V_S = V_1\left(\frac{\tau_{C1}}{\tau_{C1} - \tau_{L1}}\right)(e^{-t/\tau_{C1}} - e^{-t/\tau_{L1}}) \tag{14B}$$

where $V_1$ is the voltage on the charged capacitor $C_1$, $\tau_{C1} = RC_1$ and $\tau_{L1} = L_1/R$. Every step illustrated below may be performed with this and other similar transchest forcing functions which represent defibrillator circuitry.

To proceed with step two, from FIG. 4, nodal analysis provides an equation for $V_M$:

$$C_M \frac{dV_M}{dt} + \frac{V_M - V_3}{R_M} = 0. \quad (15)$$

Rearranging equation 15, we have $$C_M \frac{dV_M}{dt} + \frac{V_M}{R_M} = \frac{V_3}{R_M}. \quad (16)$$

Next, substituting equation 14 as an expression for $V_3$ into equation 16, the cell membrane response is now calculated as follows:

$$C_M \frac{dV_M}{dt} + \frac{V_M}{R_M} = \frac{1}{R_M}\left(\frac{V_S}{\Omega_S} + \frac{V_M}{\Omega_M}\right) \quad (17)$$

$$C_M \frac{dV_M}{dt} + \frac{V_M}{R_M} - \frac{V_M}{R_M \Omega_M} = \frac{V_S}{R_M \Omega_S} \quad (18)$$

$$C_M \frac{dV_M}{dt} + \frac{V_M}{R_M}\left(1 - \frac{1}{\Omega_M}\right) = \frac{V_S}{R_M \Omega_S}$$

Dividing through by $C_M$, and setting $\tau_M = R_M C_M$, then equation 18 becomes $$\frac{dV_M}{dt} + \frac{V_M}{\tau_M}\left(1 - \frac{1}{\Omega_M}\right) = \frac{V_S}{\tau_M}\left(\frac{1}{\Omega_S}\right). \quad (19)$$

Equation 19 is a general ordinary differential equation (ODE) that models the effects of any general forcing function $V_S$ that represents a phase of a shock pulse waveform applied across the chest. The general ODE equation 19 models the effects of a general shock pulse phase $V_S$ on the myocardium, determining cardiac cell response to such a shock pulse phase.

In the equations given below:

$C_1$ equals the capacitance of the first capacitor bank and $V_S = V_1 e^{-t/\tau_1}$;

$C_2$ equals the capacitance of the second capacitor bank and $V_S = V_2 e^{-t/\tau_2}$;

$R = R_S + R_B$, where $R_S$ = System impedance (device and electrodes);

$R_B$ = body impedance (thoracic cage, chest wall, lungs (series, parallel), heart).

To determine body impedance, $R_B$, we see that the series combination of $R_H$ and $R_{LS}$ yields $R_H + R_{LS}$. (FIG. 4). The parallel combination of $R_H + R_{LS}$ and $R_{LP}$ yields:

$$\frac{R_{LP}(R_{LS} + R_H)}{R_{LP} + R_{LS} + R_H}. \quad (20)$$

The series combination of equation 20 and $R_{CW}$ yields:

$$R_{CW} + \frac{R_{LP}(R_{LS} + R_H)}{(R_{LP} + R_{LS} + R_H)}. \quad (21)$$

The parallel combination of equation 21 and $R_{TC}$ yields:

$$R_B = \left[\frac{R_{TC}\left[R_{CW} + \frac{R_{LP}(R_{LS} + R_H)}{(R_{LP} + R_{LS} + R_H)}\right]}{R_{TC} + R_{CW} + \frac{R_{LP}(R_{LS} + R_H)}{(R_{LP} + R_{LS} + R_H)}}\right] \quad (22)$$

where $R_B$ is the impedance of the body for this model.

The discharge of a single capacitor is modeled by $V_S = V_1 e^{-t/\tau_1}$ for an initial $C_1$ capacitor voltage of $V_1$. Placing $V_S$ into equation 19 gives:

$$\frac{dV_M}{dt} + \frac{V_M}{\tau_M}\left(1 - \frac{1}{\Omega_M}\right) = \frac{V_1 e^{-t/\tau_1}}{\tau_M \Omega_S} \quad (23)$$

where $\tau_M = R_M C_M$ represents the time constant of the myocardial cell in the circuit model, and $\tau_1$, which equals $R_S C_1$, represents the time constant of $\phi_1$. Such a standard linear ODE as equation 23 has the form $$\frac{dy}{dx} + P(X)Y = Q(x).$$

These linear ODEs have an integration factor that equals $e^{pdx}$. The general solution to such equations is:

$$Y = e^{-\int pdx}\left[\int e^{\int pdx} Q dx + c\right].$$

The ODE in equation 23 models the effects of each phase of a time-truncated, capacitor-discharged shock pulse waveform. Equation 23 is a first-order linear ODE, and may be solved using the method of integration factors, to get:

$$V_{M1}(t) = ke^{-(t/\tau_M)\left(1-\frac{1}{\Omega_M}\right)} + \left(\frac{V_1}{\Omega_S}\right)\left(\frac{\tau_1}{\tau_1\left(1-\frac{1}{\Omega_M}\right) - \tau_M}\right)e^{-t/\tau_1}. \quad (24)$$

Equation 24 is an expression of cell membrane potential during $\phi_1$ of a shock pulse. To determine the constant of integration k, the initial value of $V_{M1}$ is assumed to be $V_{M1}(0) = V_G$ ("cell ground"). Applying this initial condition to equation 24, k is found to be $$k = V_G - \left(\frac{V_o}{\Omega_S}\right)\left(\frac{\tau_1}{\tau_1\left(1-\frac{1}{\Omega_M}\right) - \tau_M}\right). \quad (25)$$

Assuming $\tau_1 = RC_1$, where $R = R_S + R_B$, then the solution to the initial-value problem for $\phi_1$ is:

$$V_{M1}(t) = V_G e^{-(t/\tau_M)\left(1-\frac{1}{\Omega_M}\right)} + \left(\frac{V_1}{\Omega_S}\right)\left(\frac{\tau_1}{\tau_1\left(1-\frac{1}{\Omega_M}\right) - \tau_M}\right)\left(e^{-t/\tau_1} - e^{-(t/\tau_M)\left(1-\frac{1}{\Omega_M}\right)}\right) \quad (26)$$

Equation 26 describes the residual voltage found on a cell at the end of $\phi_1$.

Assuming $V_G = 0$ and $V_1 = 1$, the solution for cell response to an external shock pulse is $$V_{M1}(t) = \left(\frac{1}{\Omega_S}\right)\left(\frac{\tau_1}{\tau_1\left(1-\frac{1}{\Omega_M}\right) - \tau_M}\right)\left(e^{-\frac{t}{\tau_1}} - e^{-\left(\frac{t}{\tau_M}\right)\left(1-\frac{1}{\Omega_M}\right)}\right). \quad (27)$$

We may now determine optimal durations for $\phi_1$ according to criteria for desired cell response. One such design role or criterion is that the $\phi_1$ duration is equal to the time required for the external defibrillator shock pulse to bring the cell response to its maximum possible level. To determine this duration, equation 27 is differentiated and the resulting equation 27B is set to zero. Equation 27B is then solved for the time t, which represents shock pulse duration required to maximize cardiac cell response.

$$\left(\frac{AB}{\tau_M}\right)e^{-Bt/\tau_M} - \left(\frac{A}{\tau_1}\right)e^{-t/\tau_1} = 0, \quad (27B)$$

where $$A = \left(\frac{1}{\Omega_S}\right)\left(\frac{\tau_1}{\tau_1\left(1-\frac{1}{\Omega_M}\right)-\tau_M}\right)$$

and $$B = 1 - \frac{1}{\Omega_M}.$$

Solving for t, the optimal duration $d\phi_1$ for a monophasic shock pulse or $\phi_1$ of a biphasic shock pulse is found to be $$d\phi_1 = \left(\frac{\tau_1\tau_M}{\tau_1\left(1-\frac{1}{\Omega_M}\right)-\tau_M}\right)\ln\left(\frac{\tau_1\left(1-\frac{1}{\Omega_M}\right)}{\tau_M}\right), \quad (27C)$$

where "ln" represents the logarithm to the base e, the natural logarithm.

For $\phi_2$, an analysis almost identical to equations 20 through 27 above is derived. The differences are two-fold. First, a biphasic waveform reverses the flow of current through the myocardium during $\phi_2$. Reversing the flow of current in the circuit model changes the sign on the current. The sign changes on the right hand side of equation 23.

The second difference is the step taken to incorporate an independent $\phi_2$ into the charge burping model. Therefore, the $\phi_2$ ODE incorporates the $C_2$ capacitor set and their associated leading-edge voltage, $V_2$, for the $\phi_2$ portion of the pulse. Then $\tau_2$ represents the $\phi_2$ time constant; $\tau_2=RC_2$, and $V_S=-V_2 e^{-t/\tau_2}$. Equation 23 now becomes:

$$\frac{dV_M}{dt} + \left(\frac{V_M}{\tau_M}\right)\left(1-\frac{1}{\Omega_M}\right) = \frac{-V_2 e^{-t/\tau_2}}{\tau_M \Omega_S}. \quad (29)$$

Equation 29 is again a first-order linear ODE. In a similar manner, its general solution is determined to be:

$$V_{M2}(t) = ke^{(-t/\tau_M)(1-\frac{1}{\Omega_M})} - \left(\frac{V_2}{\Omega_S}\right)\left(\frac{\tau_2}{\tau_2\left(1-\frac{1}{\Omega_M}\right)-\tau_M}\right). \quad (30)$$

To determine the constant of integration k, the value of $V_{M2}$ at the end of $\phi_1$ is $$V_{M2}(0) = V_{M1}(d_{\phi 1}) = V_{\phi 1}. \quad (31)$$

where $d_{\phi 1}$ is the overall time of discharge for $\phi_1$ and $V_{\phi 1}$ is the voltage left on the cell at the end of $\phi_1$. Applying the initial condition to equation 30 and solving for k:

$$k = V_{\phi 1} + \left(\frac{V_2}{\Omega_S}\right)\left(\frac{\tau_2}{\tau_2\left(1-\frac{1}{\Omega_M}\right)-\tau_M}\right). \quad (32)$$

The solution to the initial-value problem for $\phi_2$ is $$V_{M2}(t) = \left(\frac{V_2}{\Omega_S}\right)\left(\frac{\tau_2}{\tau_2\left(1-\frac{1}{\Omega_M}\right)-\tau_M}\right)\left(e^{-(t/\tau_M)(1-\frac{1}{\Omega_M})} - e^{-t/\tau_2}\right) + V_{\phi 1} e^{-(t/\tau_M)(1-\frac{1}{\Omega_M})}. \quad (33)$$

Equation 33 provides a means to calculate the residual membrane potential at the end of $\phi_2$ for the cells that were not stimulated by $\phi_1$. Setting Equation 33 equal to zero, we solve for t, thereby determining the duration of $\phi_2$, denoted $d\phi_2$, such that $V_{M2}(d\phi_2)=0$. By designing $\phi_2$ with a duration $d\phi_2$, the biphasic shock pulse removes the residual change placed on a cell by $\phi_1$. We determine $d\phi_2$ to be:

$$d_{\phi 2} = \left(\frac{\tau_2\tau_M}{\tau_2\left(1-\frac{1}{\Omega_M}\right)-\tau_M}\right)\cdot\ln\left(1+\left(\frac{\tau_2\left(1-\frac{1}{\Omega_M}\right)-\tau_M}{\tau_2}\right)\left(\frac{\Omega_S V_{\phi 1}}{V_2}\right)\right). \quad (34)$$

From the equations above, an optimal monophasic or biphasic defibrillation waveform may be calculated for an external defibrillator.

As an example, an external defibrillator may be designed as set forth below. Assume a monophasic truncated exponential shock pulse, a 200 $\mu$F capacitor, so that $\tau_1$=R·(200 $\mu$F). Suppose also that the external defibrillator is designed to apply the maximal cardiac cell response design rule (equation 27C) to determine the duration of the discharge. Suppose further that the human cardiac cell time constant is estimated to be 3±1 ms. Further assume that the external defibrillator energy source comprises five 1000 $\mu$F capacitors in series to implement a 200 $\mu$F capacitor bank. If each capacitor is charged to 400V, for a total of 2000V for the leading-edge voltage, this represents 400 J of stored energy. The transchest elements are estimated at: 82% current through the thoracic cage; 14% through the chest wall and lungs in parallel; and 4% of applied current through the lung in series with the heart. Then the membrane resistance coefficient $\Omega_M$=5.9, and the system resistance coefficient $\Omega_S$=2.3 Then the table below illustrates the application of the design rule as the overall chest resistance ranges from 25Ω to 200Ω:

| R (Ω) | $\tau_1$ | d($\phi_1$) | $V_{final}$ | $E_{delivered}$ |
|---|---|---|---|---|
| 25 | 5.2 | 5.05 | 757 | 343 |
| 50 | 10.2 | 6.90 | 1017 | 297 |
| 75 | 15.2 | 8.15 | 1170 | 263 |
| 100 | 20.2 | 9.10 | 1275 | 238 |
| 125 | 25.2 | 9.90 | 1350 | 216 |
| 150 | 30.2 | 10.55 | 1410 | 201 |
| 175 | 35.2 | 11.15 | 1457 | 186 |
| 200 | 40.2 | 11.65 | 1497 | 176 |

It should be noted and understood that the design of $\phi_2$ is independent from $\phi_1$. To design $\phi_2$, the only information necessary from $\phi_1$ is where the cell response was left when $\phi_1$ was truncated. Additionally, $\phi_2$ need not use the same or similar circuitry to that used for $\phi_1$. For example, $\phi_2$ may use a model as illustrated in FIG. 5B where $\phi_1$ may use the model illustrated in FIG. 5A or vice versa.

DESCRIPTION OF THE PRESENT INVENTION

From Equations 27, 27C, 33, and 34 above it is evident that the characteristics of the cell membrane responses are functionally related to the defibrillator time constants $\tau_1$ and $\tau_2$, and to the time constant of the cell membrane $\tau_M$. Time constants $\tau_1$ and $\tau_2$ are established by the capacitance of the capacitors $C_1$ and $C_1$ and the electrode system resistance $R_S$. It has been determined that efficacious and relatively low energy biphasic external defibrillation pulses can be generated from relatively low capacitance capacitors if the phase-duration ratio ($d_{\phi 2}/d_{\phi 1}$) is optimized to meet certain criteria described below.

Figures 6A, 6B:
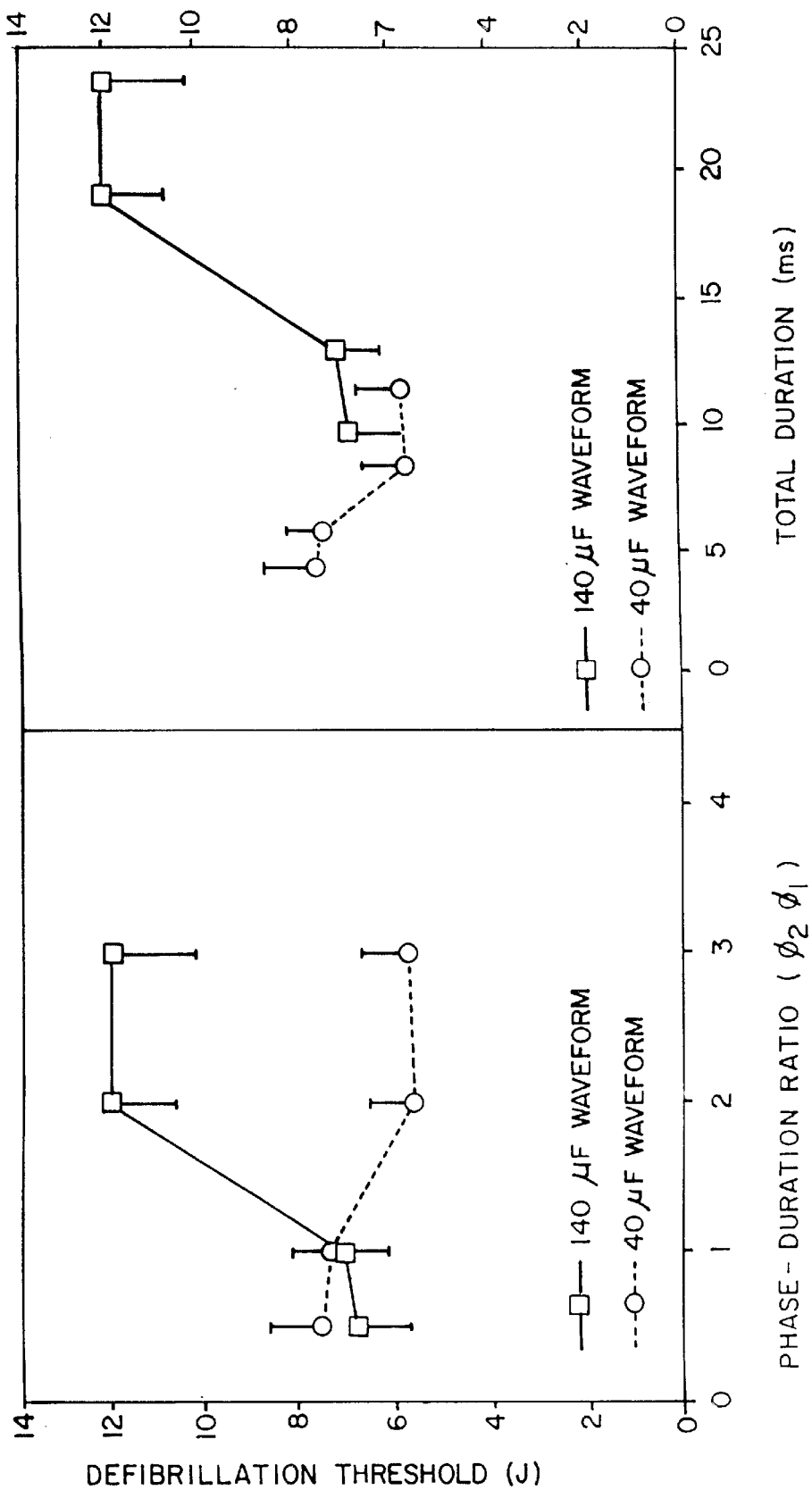
FIG. 6A is a graph of phase-duration ratio as compared to defibrillation threshold.
FIG. 6B is a graph of total duration as compared to defibrillation threshold.

FIG. 6A is a graph of experimentally derived intra cardiac defibrillation thresholds (DFTs) as a function of biphasic defibrillation pulse phase-duration ratios for pulses generated from both 140 μF and 40 μF capacitors. The defibrillation threshold is statistically computed from the experimental data and is the defibrillation pulse energy at a 50% effective defibrillation dose. It is evident from FIG. 6A that, with phase-duration ratios greater than one, efficacious biphasic defibrillation pulses having relatively low energy levels can be generated from 40 μF capacitors. In comparison, similar biphasic defibrillation pulses having these phase-duration ratios and generated from 140 μF capacitors required relatively high energy levels to achieve the same efficacy.

FIG. 6B is a graph of experimentally derived intra cardiac defibrillation thresholds as a function of total pulse duration (i.e., both phases one and two) for pulses generated from both the 140 μF and 40 μF capacitors. From this figure it is evident that at the lowest defibrillation thresholds, the durations of biphasic defibrillation waveforms produced by both the 140 μF and 40 μF capacitors are similar. However, the intra cardiac biphasic defibrillation waveforms generated by the 140 μF capacitor with the shorter total durations and small phase duration ratios have higher thresholds. Further, the intra cardiac biphasic defibrillation waveforms generated by the 140 μF capacitor with the longer total durations and larger phase duration ratios have the highest defibrillation thresholds.

Figure 7:
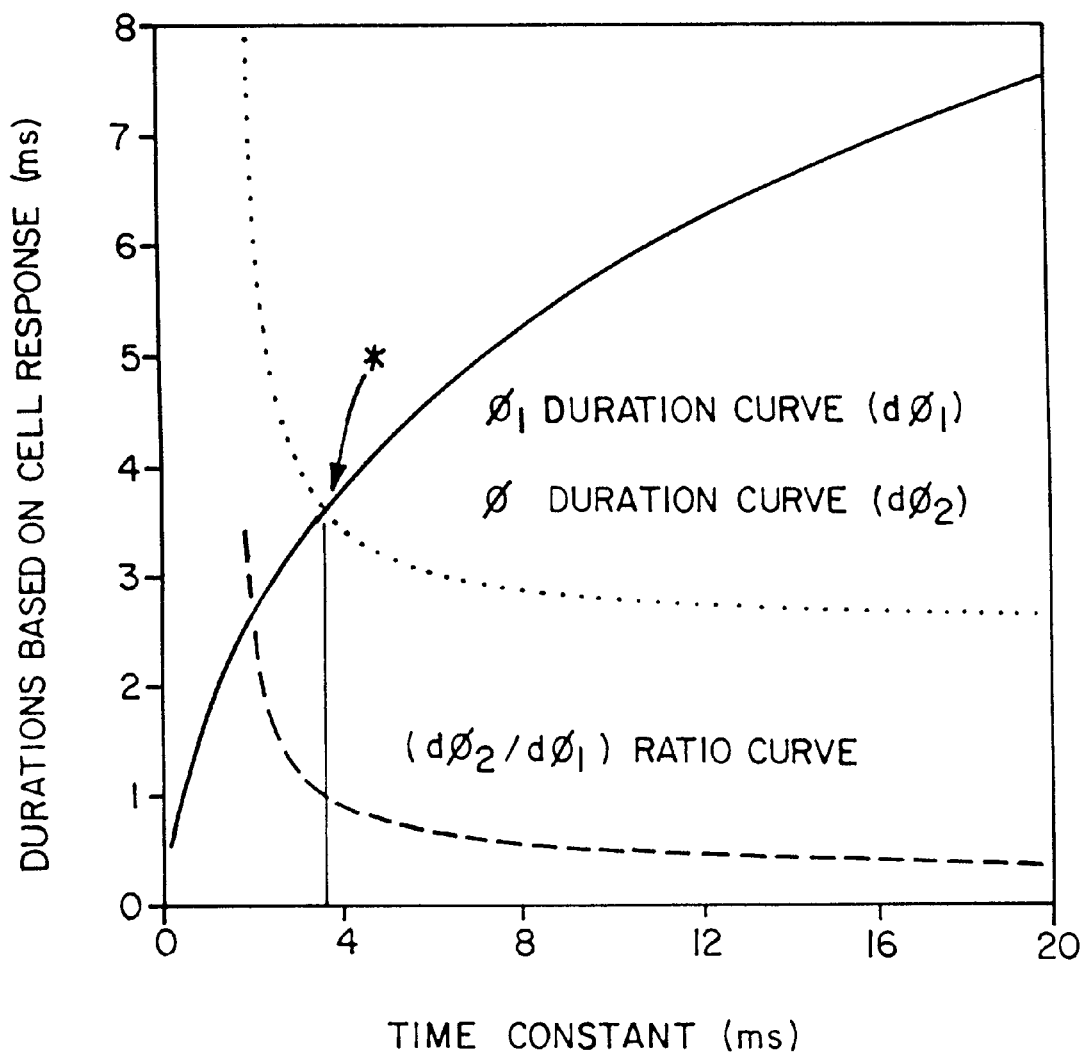
FIG. 7 is a graph of system time constant and capacitance as compared to both optimal duration and phase duration ratio.

FIG. 7 is a graph of optimal first and second phase pulse component durations ($D_{\phi 1}$ and $d_{\phi 2}$) and the optimal phase-duration ratio ($d_{\phi 2}/d_{\phi 1}$) as a function of both the capacitance of the capacitor used to generate the pulse component and the defibrillator time constant. The capacitance values on the graph are scaled to the pulse component durations and phase-duration ratios on the basis of a 50Ω defibrillator-patient resistance. The total duration of the defibrillation pulse is the sum of the first and second phase pulse components.

From the information represented in FIGS. 6A, 6B and 7, it has been determined that for a given pulse generation capacitor such as $C_1$ and $C_2$ having relatively small values (i.e., less than about 100 μF) and where $\tau_1$ and $\tau_2$ are less than $\tau_M$, preferred biphasic external defibrillation waveforms will have a phase-duration ration ($d_{\phi 2}/d_{\phi 1}$) greater than one. Particularly efficacious external defibrillation waveforms meeting these requirements will be provided most preferably from pulse generation capacitors of less than about 60 μF. For the higher resistance patient the pulse generation capacitors may be less than 40 μF. Furthermore, particularly efficacious external defibrillation waveforms meeting these requirements will have a phase-duration ratio ($d_{\phi 2}/d_{\phi 1}$)≧1.5. The table below illustrates capacitor values for a range of resistance values.

| R (Ω) | Cap (μF) |
| --- | --- |
| 50 | 72 |
| 60 | 60 |
| 70 | 50 |
| 80 | 45 |
| 90 | 40 |
| 100 | 36 |
| 110 | 32 |
| 120 | 30 |
| 130 | 28 |
| 140 | 26 |
| 150 | 24 |

Each row entry represents the point marked * in FIG. 7, for a fixed resistance value, and as determined from equations 27, 27C, 33 and 34. More than 90% of external defibrillation shocks are applied across a patent load from 60Ω to 90Ω, and thereby demonstrating that pulse generation capacitors of less than about 60 μF are optimally suited for external defibrillation.

Although the present invention has been described with reference to preferred embodiments, worked skilled in the art will recognize that changes may be made in form and detail without departing from the spirit and scope of the present invention.

What is claimed is:

1. An external defibrillator for delivering a truncated waveform having a first waveform phase and a second waveform phase, the defibrillator having a first charge storage component, a first truncating switch connected in series with the first charge storage component, a second charge storage component, a second truncating switch connected in series with the second charge storage component, waveform control circuitry connected to the first and second truncating switches for independently operating the first and second truncating switches, and a pair of external electrodes connected to the waveform control circuitry wherein the waveform control circuitry controls the first and second truncating switches such that the duration of the second phase waveform delivered by the second charge storage component is greater than the duration of the first phase waveform delivered by the first charge storage component.

2. The defibrillator of claim 1 wherein the first and second charge storage components are selected such that the duration of the second phase waveform is at least fifty percent greater than the duration of the first phase waveform.

3. The defibrillator of claim 1 wherein the first and second charge storage components are selected such that the duration of the second phase waveform is at least twice the duration of the first phase waveform.

4. An external defibrillator for delivering a truncated damped sinusoidal waveform having a first waveform phase and a second waveform phase, the defibrillator having a first charge storage component, a first inductive component connected in series with the first charge storage component, a first truncating switch connected in series with the first charge storage component and the first inductive component, a second charge storage component, a second inductive component connected in series with the second charge storage component, a second truncating switch connected in series with the second charge storage component and the second inductive component, waveform control circuitry connected to the first and second truncating switches for independently operating the first and second truncating switches, and a pair of electrodes connected across the first and second circuits, the defibrillator comprising:

the waveform control circuitry controlling the first and second truncating switches such that the duration of the second phase waveform delivered by the second charge storage component is greater than the duration of the first phase waveform delivered by the first charge storage component.

5. The defibrillator of claim 4 wherein the duration of the second phase waveform is at least fifty percent greater than the duration of the first phase waveform.

6. The defibrillator of claim 4 wherein the duration of the second phase waveform is at least twice the duration of the first phase waveform.

7. An external defibrillator for applying a truncated waveform having a first waveform phase and a second waveform phase, the defibrillator having first and second pulse generation capacitors, a first truncating switch connected in series with the first pulse generation capacitor, a second truncating switch connected in series with the second pulse generation capacitor, waveform control circuitry connected to the first and second truncating switches for independently operating the waveform control circuitry wherein the first and second pulse generation capacitors are less than about 100 μF.

8. The external defibrillator of claim 7 wherein the first and second pulse generation capacitors are less than or equal to 60 μF.

9. The external defibrillator of claim 7 wherein the first and second pulse generation capacitors are less than or equal to 40 μF.

10. The external defibrillator of claim 7 further comprising measuring means for measuring a patient dependent parameter from which a patient cell membrane time constant is determinable, and wherein the external defibrillator contains a resistance, wherein the first and second pulse generation capacitors have time constants, said time constants being less than the determinable patient cell membrane time constant.

11. A method for externally defibrillating the heart of a patient having heart cell membranes characterized by a time constant $\tau_M$, the method of defibrillating including the steps of:

providing an electrode system including a pair of external electrodes and characterized by a resistance $R_S$;

positioning the electrodes on the chest of a patient;

providing a first capacitor set characterized by a capacitance $C_1 < 100$ μF where $R_S C_1 = \tau_S < \tau_M$;

charging the first capacitor set to a charge potential; and discharging the first capacitor set through the electrode system to provide a first phase component defibrillation pulse having a first polarity and a first duration.

12. The method of claim 11 wherein providing the first capacitor set includes providing a capacitor set characterized by a capacitance $C_1 \leq 60$ μF.

13. The method of claim 11 wherein providing the first capacitor set includes providing a capacitor set characterized by a capacitance $C_1 \leq 40$ μF.

14. The method of claim 11 further including the steps of:

providing a second capacitor set characterized by a capacitance $C_2 < 100$ μF where $R_S C_2 = \tau_S < \tau_M$;

charging the second capacitor set to a charge potential; and discharging the second capacitor set through the electrode system after discharging the first capacitor set to provide a second phase component defibrillation pulse having a second polarity and a second duration, wherein the discharging of the second capacitor set causes the second duration which is greater than the first duration.

15. The method of claim 14 wherein providing the first and second capacitor sets includes providing first and second capacitor sets characterized by capacitances $C_1$ and $C_2 \leq 60$ μF.

16. The method of claim 14 wherein providing the first and second capacitor sets includes providing first and second capacitor sets characterized by capacitances C1 and $C_1 \leq 40$ μF.

17. The method of claim 14 wherein the discharging of the second capacitor set causes the second duration which is at least about twice the first duration.

18. The method of claim 14 wherein the discharging of the second capacitor set causes the second duration which is at least about 50% greater than the first duration.

19. The method of claim 14 wherein the discharging of the second capacitor set causes the second duration which is greater than the first duration.

20. An external defibrillator for applying a damped sinusoidal waveform having a first waveform phase and a second waveform phase to a pair of electrodes, the electrodes being in electrical communication with a patient, the patient having a certain cell membrane time constant, the external defibrillator having pulse generation capacitor means, the defibrillator comprising:

the pulse generation capacitor means being less than 100 μF.

21. The external defibrillator of claim 20 wherein the pulse generation capacitor means are less than 60 μF.

22. The external defibrillator of claim 20 wherein the pulse generation capacitor means are less than 40 μF.

23. The external defibrillator of claim 20 wherein the pulse generation capacitor means have a time constant, said time constant being less than the patient cell membrane time constant.

24. An external defibrillator for applying a damped sinusoidal waveform having a first waveform phase and a second waveform phase to a pair of electrodes, the electrodes being in electrical communication with a patient, the patient having a certain cell membrane time constant, the external defibrillator having pulse generation capacitor means, the defibrillator comprising:

the pulse generation capacitor means having a first capacitor and a second capacitor, the first capacitor being less than 100 μF and the second capacitor being less than 100 μF.

25. The external defibrillator of claim 24 wherein the first capacitor is less than 60 μF and the second capacitor is less than 60 μF.

26. The external defibrillator of claim 24 wherein the first capacitor is less than 40 μF and the second capacitor is less than 40 μF.

27. The external defibrillator of claim 24 wherein the first capacitor has a time constant, said time constant being less than the patient cell membrane time constant, and wherein the second capacitor has a time constant, said time constant being less than the patient cell membrane time constant.

* * * * *